US006063982A

United States Patent [19]
Martin et al.

[11] Patent Number: 6,063,982
[45] Date of Patent: May 16, 2000

[54] PERSONAL HYGIENE ARTICLES FOR ABSORBING FLUIDS

[75] Inventors: Bruce D. Martin, DeRidder, La.; Thomas L. Wiesemann; John D. Shoemaker, Jr., both of Mobile, Ala.

[73] Assignee: International Paper Company (from Thomas L. Wiesemann and John J. Shoemaker Jr.), Purchase, N.Y.

[21] Appl. No.: 08/924,149

[22] Filed: Sep. 5, 1997

Related U.S. Application Data

[62] Division of application No. 08/499,115, Jul. 6, 1995, Pat. No. 5,766,159.

[51] Int. Cl.$^7$ ....................................................... A61F 13/15
[52] U.S. Cl. ............................................. 604/374; 604/358
[58] Field of Search .................................. 604/368–378, 604/358

[56] References Cited

U.S. PATENT DOCUMENTS

| | | |
|---|---|---|
| 1,310,694 | 7/1919 | Edwardes . |
| 2,683,088 | 7/1954 | Reynolds . |
| 2,880,726 | 4/1959 | Stieg . |
| 3,057,037 | 10/1962 | Carney et al. . |
| 3,105,491 | 10/1963 | Harwood . |
| 3,658,613 | 4/1972 | Steiger . |
| 3,661,154 | 5/1972 | Torr . |
| 3,670,731 | 6/1972 | Harmon . |
| 3,739,782 | 6/1973 | Bernardin . |
| 3,809,604 | 5/1974 | Estes . |
| 3,897,782 | 8/1975 | Tunc . |
| 4,096,289 | 6/1978 | Nischwitz et al. . |
| 4,103,062 | 7/1978 | Aberson et al. . |
| 4,104,214 | 8/1978 | Meierhoefer . |
| 4,105,033 | 8/1978 | Chatterjee et al. . |
| 4,165,743 | 8/1979 | Denning . |
| 4,242,242 | 12/1980 | Allen . |
| 4,340,556 | 7/1982 | Ciencewicki . |
| 4,444,830 | 4/1984 | Erickson . |
| 4,689,118 | 8/1987 | Makoui et al. . |
| 4,767,848 | 8/1988 | Makoui et al. . |
| 4,888,093 | 12/1989 | Dean et al. . |
| 4,911,700 | 3/1990 | Makoui et al. . |
| 4,919,681 | 4/1990 | Tyler et al. . |
| 5,019,063 | 5/1991 | Marsan et al. . |
| 5,071,681 | 12/1991 | Manning et al. . |
| 5,091,240 | 2/1992 | Kajander et al. . |
| 5,147,343 | 9/1992 | Kellenberger . |
| 5,413,747 | 5/1995 | Akers et al. . |
| 5,478,335 | 12/1995 | Colbert . |

OTHER PUBLICATIONS

Rydholm, Sven A., *Pulping Processes*, Interscience Publishers, 1965.

*Primary Examiner*—John G. Weiss
*Assistant Examiner*—Dennis Ruhl
*Attorney, Agent, or Firm*—Luedeka, Neely & Graham, P.C.

[57] ABSTRACT

A personal hygiene article having an increased capacity for absorbing fluids is disclosed. The article contains a surface layer containing at least one fluid permeable material and a sublayer containing at least about 10 wt. % of a fluffed wood pulp for retaining fluids. Articles of the invention have improved absorbance properties under re-wet conditions even in the absence of organic cross-linking agents or fiber modifiers.

15 Claims, No Drawings

PERSONAL HYGIENE ARTICLES FOR ABSORBING FLUIDS

This application is a division of application Ser. No. 08/499,115, filed Jul. 6, 1995, now U.S. Pat. No. 5,766,159.

FIELD OF THE INVENTION

This invention relates to personal hygiene articles for absorbing fluids, and more particularly to personal hygiene articles containing low cost highly absorbent materials.

BACKGROUND OF THE INVENTION

Personal hygiene articles which are designed to absorb fluids, particularly body fluids such as blood, urine, pus and the like, include items such as tampons, sanitary napkins, diapers, bibs, incontinence pads, surgical sponges, compresses, bandages, and wipes. An important component of these articles is the absorbent material, generally known as fluff, which may be made from cellulosic fibers or synthetic fibers or a combination of cellulosic and synthetic fibers. As used in these articles, fluff is intended to provide one of two functions, to wick fluid away from the surface of the article and transport the fluid to an internal location within the product away from the surface of the article or to absorb and retain an amount of fluid so that the surface of the article remains dry. Fibers may be formed with different properties depending on which of the two functions is more desirable. Cellulosic fibers may be used as fluff in these articles because they are relatively inexpensive and are typically inert to human body chemistry, thus they do not create any unwanted side effects associated with their use.

It has long been a goal of the fiber processing industry, and the industries which they supply, to develop improved fiber structures that can transport and retain an increased amount of fluid at a higher rate of absorbency. Additionally, the ability to handle several repeated instances of fluid wetting and transport is seen as greatly desirable for many personal hygiene products, as exemplified by a diaper intended for overnight use.

The most desirable fibers for use as fluff in disposable personal hygiene articles are cellulosic fibers of wood prepared according to conventional techniques. Such fibers are readily available and are low cost. Unfortunately, commercially available cellulosic fibers have a tendency to bond together as they dry after an initial wetting. Bonding of the fibers causes the fluff to clump into a mass that is no longer able to absorb and transport liquid in the amount or at the rate observed during the first wetting. Accordingly, the performance of known cellulosic fibers is less than optimal for the personal hygiene articles made containing such fibers.

In response to this problem, various modifications of the fibers have been devised which are intended to enhance the multiple wetting transport properties of the fluff in personal hygiene articles. Unfortunately, these modifications tend to have significant deficiencies, not the least of which is the increased cost of manufacturing. Additionally, fibers treated with organic compounds to improve their transport properties may give off formaldehyde or other residues of the organic cross-linking agents or catalysts which cannot be completely removed from the fibers. Thus, personal hygiene articles containing organically treated fibers may release unpleasant odors or they may increase the amount of skin irritation associated with the articles. Furthermore, the extreme process conditions and length of time required for treating the fibers are significant deficiencies of the currently used methods for increasing the fluid transport properties of cellulosic fibers.

Thus, there is a need for personal hygiene articles containing inexpensively processed, absorbent fibers. The fibers should have fluid transport properties which remain effective to transport and retain fluids even upon repeated wetting and/or compression of the fibers. Furthermore, the fibers should be substantially free of skin irritants and/or odor releasing substances.

Accordingly, it is an object of the present invention to provide an improved personal hygiene article for absorbing fluids.

It is another object of the invention to provide an improved personal hygiene article containing a cellulosic fiber fluff having improved fluid transport properties.

It is a further object of the invention to provide an improved personal hygiene article containing a wood fiber fluff for transporting and retaining fluids in a location away from the surface of the article.

It is yet another object of the invention to provide an improved personal hygiene article wherein the fiber fluff retains its fluid transport and fluid retention properties through several wetting episodes even after compression of the fibers.

SUMMARY OF THE INVENTION

Having regard to the above and other objects and advantages, the present invention provides an improved personal hygiene article for absorbing fluids. The personal hygiene article comprises a surface layer containing at least one fluid permeable material and a sublayer adjacent the surface layer containing at least about 10 wt. % of fluffed wood pulp for retaining fluids. The sublayer may be further characterized as having a pre-poured saturated drainage (PSD) capacity greater than about 400 mL. A significant benefit of the articles of the present invention are that they have an increased capacity to absorb, transport and retain fluids even after being previously wet and compressed.

Accordingly, it has been found that wood fibers, preferably softwood fibers, having been treated with a strong base under low temperature conditions (e.g., temperatures in the range of from about 0° C. to about 80° C.) have an unexpectedly high dynamic capacity for absorbing fluids in personal hygiene articles. The base-treated wood fibers used to form the absorbent sublayer of the personal hygiene articles of the present invention have been found to retain fluids to a greater degree than do the untreated fibers. Also, the base-treated fibers, hereinafter referred to as "fluffed wood pulp" do not give off formaldehyde or other residues of organic compounds typically used for increasing the transport properties of the fibers since the fibers need not be treated with organic cross-linking agents and the like to improve their absorbency properties. Furthermore, personal hygiene articles containing a fluffed wood pulp sublayer have been found to be capable of repeated wetting and absorbing episodes without substantial binding or clumping of the fluffed wood pulp even after compression of the sublayer.

DETAILED DESCRIPTION OF THE INVENTION

Personal hygiene articles of the invention containing highly absorbent fluffed wood pulp include diapers, tampons, sanitary napkins, bibs, incontinence pads, surgical sponges, compresses, bandages, wipes, and the like. Personal hygiene articles of the foregoing type typically contain a first layer made of at least one fluid permeable material and a sublayer adjacent the first layer containing from about 10 to about 100 wt. % of fluffed wood pulp as the absorbent layer. In a preferred form of the invention, the personal hygiene article will contain at least one fluid permeable topsheet layer, at least one fluid impervious backsheet layer coterminous with the topsheet layer and at least one absorbent sublayer between the topsheet layer and the backsheet layer, wherein the absorbent sublayer contains from about 10 up to about 100 wt. % of fluffed wood pulp having a pre-poured saturated drainage capacity greater than about 400 mL.

Both the fluid permeable material and the fluid impervious material, when used, are well known to those of ordinary skill. Accordingly, the topsheet layer may be made from a wide range of materials, such as porous foams, reticulated foams, appertured plastic films, natural fibers (e.g., wood or cotton fibers), synthetic fibers (e.g., polyester or polypropylene fibers) or from a combination of natural and synthetic fibers. Preferably, the fluid permeable material is a hydrophobic material which will effectively isolate the wearer's skin from fluids in the absorbent sublayer. The fluid permeable material in the topsheet layer may be treated with a surfactant in order to facilitate penetration of fluid through the layer, recognizing, of course, that the topsheet layer should remain relatively hydrophobic as compared to the absorbent sublayer.

In one of its embodiments, the present invention relates to a method for making a personal hygiene article. The method comprises treating a wood pulp with an amount of base at a temperature within the range of from about 0° to about 80° C. thereby forming a treated wood pulp having a pre-poured saturated drainage (PSD) capacity greater than about 400 mL. Next the treated wood pulp is fluffed to form a highly absorbent sublayer for use in the article. At least one surface of the sublayer is then laminated with a topsheet formed from a flexible, fluid permeable material thereby forming the personal hygiene article. In a particularly preferred embodiment, a second surface of the sublayer is laminated with a backsheet formed from a fluid impervious material so that the absorbent sublayer is between the topsheet layer and the backsheet layer. The backsheet layer is preferably made from a thin plastic polyolefinic film that is relatively impervious to fluids. Accordingly, the backsheet layer is selected from a material which effectively prevents fluids absorbed by the absorbent sublayer from wetting articles of clothing and the like which contact th personal hygiene article. Preferably, the backsheet layer is a polyethylene film having a thickness of from about 0.012 mm to about 0.051 centimeters. However, any commercially available fluid impervious material having suitable flexibility may be used to make the backsheet layer.

Well known fluid permeable materials, fluid impervious materials and methods for assemblage of personal hygiene articles containing a topsheet layer, a backsheet layer and an absorbent layer are disclosed in U.S. Pat. No. 5,019,063, incorporated herein by reference as if fully set forth. However, in contrast to the personal hygiene articles disclosed in the foregoing and other references, the articles of the present invention contain a one or more layers of highly absorbent fluffed wood pulp as the absorbent sublayer. The absorbent sublayer of the present invention may be characterized not only by its outstanding pre-poured drainage capacity of greater than about 400 mL but also by its strike-through acquisition re-wet weight of less than about 40 grams.

Accordingly, the absorbent sublayer of the personal hygiene articles of the present invention contain one or more layers of fluffed wood pulp which may or may not be separated by tissue or nonwoven materials. The absorbent sublayer may contain from about 10 up to about 100 wt. %, preferably from about 20 to about 100 wt. % of the fluffed wood pulp, and most preferably about 50 wt. % fluffed wood pulp and about 50 wt. % unprocessed fiber. Optionally, the absorbent sublayer may be composed of from about 10 to about 90 wt. % of fluffed wood pulp and from about 10 to about 90 wt. % of super-absorbing polymers in the form of grains, powders, small filaments or other forms. Super-absorbing polymers may be admixed with the fluffed wood pulp or they may be placed in a separate absorbent layer above or below the fluffed wood pulp layer to form a composite absorbent sublayer.

Unlike the materials known in the prior art, articles of the present invention containing fluffed wood pulp are capable of maintaining their excellent fluid transport properties and fluid retention characteristics even after repeated wetting and absorbing episodes. The improved fluid transport properties of the articles of the present invention may be due, at least in part, to the fact that the fibers of the fluffed wood pulp have a decreased tendency to bind or clump together upon wetting drying, even when compressed by body weight.

The fluffed wood pulp for use in the absorbent sublayer of the articles of the present invention may be made by combining an amount of water with a cellulosic wood fiber selected from the group consisting of bleached and unbleached softwood, hardwood, and bagasse, preferably bleached softwood fiber to form a slurry. The amount of water combined with the wood fibers is that amount which is sufficient to form a slurry having a consistency in the range of from about 0.1 to about 88 wt. %, and preferably in the range of from about 8 to about 40 wt. %. Consistency is defined as the oven dry weight of the wood fibers in the slurry, divided by the total weight of the slurry.

After forming the slurry, the slurry is treated with a basic solution formed by combining NaOH, KOH, LiOH, $NH_4OH$, $Na_2CO_3$, white liquor (e.g., caustic solution containing $Na_2S$ and $Na_2CO_3$), or a combination of two or more of the foregoing compounds or mixtures with an amount of polar solvent such as water. The treatment effectiveness is dependent on both the concentration of the basic solution and the temperature. At lower temperatures, weaker basic solutions may be used to achieve a similar effect. Accordingly, preferred treatment temperatures are in the range of from about 20° to about 80° C. and the concentrations of the corresponding basic solutions are preferably in the range of from about 100 to about 350 grams per liter respectively.

While the treatment of the pulp with a basic solution is relatively independent of the slurry consistency, lower consistencies may require more basic solution in order to maintain the desired base concentration. Furthermore, slurry consistencies of about 30 wt. % or higher may require more elaborate mixing techniques in order to assure adequate contact between the wood fibers in the slurry and the strong base.

Required treatment times are relatively short, although treatment of the wood fibers with the strong base may be conducted for 10 hours or more if desired. Typically, the wood fibers are treated for a period of time from about 10 seconds to about 1 hour, more preferably from about 30 seconds to about 30 minutes and most preferably from about 1 minute to about 5 minutes. During treatment, the wood fibers and strong basic solution are admixed vigorously to assure adequate contact and reaction between the fibers and the basic solution.

Treatment of the wood fibers may be conducted under atmospheric, subatmospheric or superatmospheric conditions. For ease of equipment design and operation, atmospheric conditions are most preferred.

Starting with equations defining concentration and consistency, knowing the oven dry weight of the fiber, the weight of the water in the slurry, the base concentration and slurry consistency desired, the amount of water and base to use in preparing the basic treating solution can be calculated. In order to illustrate the calculations, the following example is given. In this example, it is assumed that the basic solution for treating the fibers is made from water and solid NaOH.

EXAMPLE 1

In order to determine the desired consistency of the pulp slurry, the following equation may be used:

$$C_s = W_f/(W_f + W_{wp} + W_{wc} + W_c)$$

where $C_s$=Consistency of the slurry (wt. %),
$W_f$=Oven dry weight of cellulosic fibers in the slurry (grams),
$W_{wp}$=Weight of water in the slurry (grams),
$W_{wc}$=Weight of water in the basic solution (grams),
$W_c$=Weight of base in the basic solution (grams).

In order to determine the concentration of the basic solution, the following equation may be used:

$$C_c = W_c/(W_{wp} + W_{wc})$$

where $C_c$=Concentration of base in the slurry (grams/ml).

The total weight of the slurry is defined by the following equations:

$$W_p = W_{wp} + W_f$$

where $W_p$=Total weight of the slurry (grams)

and $$C_p = W_f/W_p$$

where $C_p$=Consistency of the slurry (wt. %).

Solving the foregoing equations for $W_{WC}$, the weight of the water required, and $W_c$, the weight of the base in the solution, yields the following equations:

$$W_{wc} = W_p(C_p((1/C_s - 1)/(C_c + 1)) + (C_p - 1))$$

and $$W_c = C_c W_p C_p(1/C_s - 1)/(C_c + 1).$$

Throughout this example, it is assumed that one milliliter of water always weighs one gram although 1 ml of basic solution weighs more than 1 g.

Treatment of the wood fibers requires a greater base concentration at higher temperatures, and so the concentration chosen for the treatment solution will depend upon the temperature at which the treatment is conducted. The following example illustrates the relationship between the base concentration and temperature useful for preparing fluffed wood pulp for use in the articles of the present invention.

EXAMPLE 2

The following strong base concentrations of NaOH correspond to treatment temperatures found to be suitable for preparing fluffed wood pulp for use in an absorbent sublayer:

| Temperature, ° C. | Concentration of NaOH (g/L) |
|---|---|
| 22 | 120 |
| 48 | 165 |
| 64 | 223 |
| 74 | 330 |

Both the wood fibers and the basic solution may be brought to or cooled below the desired treatment temperature before the fibers are treated. Likewise, the basic solution may be super-cooled so that the desired treatment temperature is not exceeded when the basic solution is admixed with hot pulp. For example, for treatment of wood pulp at a temperature 74° C., a strong basic solution will typically need to be cooled to about 22° C. before admixing the strong basic solution with the pulp.

In order to terminate the treatment of the wood fibers, water may be added to the slurry in an amount sufficient to decrease the basic solution to a concentration of less than about 100 grams per liter. In the alternative, the temperature of the slurry containing the treated wood fibers and basic solution may be increased above about 80° C. in order to terminate the treatment. Any combination of water addition and temperature increase may also be used to terminate the treatment reaction.

Once treated, excess water may be drained from the mixture, and the remaining treated wood fibers may be washed one or more times with a rinse water and/or an acidic solution to further remove and/or neutralize the basic solution. The water wash should be sufficient to dilute the basic solution to below the effective treatment range, e.g. the concentration of base in the pulp should be less than about 100 grams per liter. Repeated washings with water may be required to effectively dilute the basic solution. Accordingly, the slurry of treated wood fibers may be rinsed and/or neutralized until the pH of the washings is in the range of from about 1 and to about 10, and preferably from about 3 to 9. The washings may be aided by pressing the pulp to remove excess liquid. In the alternative, the pulp may be washed with water and treated with an acid solution such as a sulfuric acid solution to reduce the total number of water washings required to decrease the base concentration in the treated wood fibers.

The fluffed wood pulp may then be recovered from the treatment slurry and dried in either sheet form or in free form. Preferably, the fibers are dried and formed such that they may be used on the equipment employed to produce the personal hygiene articles without any modification to the equipment. In an alternate embodiment, the fluffed wood pulp may be combined with unprocessed fibers to form a blend for use in the absorbent sublayer. Alternatively, treated fibers may be obtained commercially as by purchasing fluffed wood pulp from Buckeye Cellulose Corporation.

Without being bound by theory, it is believed that the fluffed wood pulp fibers are more irregularly shaped than fibers not treated with a low temperature basic solution. The untreated fibers are believed to be relatively linear and align with each other during episodes of wetting. Upon drying, untreated fibers bind to one another. However, the irregularly shaped fluffed wood pulp fibers do not align upon wetting and, thus, do not bind or clump during drying.

The wood fibers treated by the foregoing process not only have an increased fluid absorbency, but the fluffed wood pulp also has increased fluid transport properties and a superior ability to retain these enhanced characteristics through successive wetting and drying cycles.

Fluffed wood pulp having increased absorbency and fluid transport properties may be assembled with other materials into personal hygiene articles according to the following method. A fluid permeable topsheet material may be prepared from a flexible apertured polymeric film. The topsheet material may include one or more layers of standard nonwoven materials or tissues known in the art. Next, a fluid impervious backsheet material is selected from a flexible second polymeric film. One or more layers of fluffed wood pulp are placed between the layers of the topsheet and backsheet materials. The perimeter edges of the topsheet and backsheet materials may then be secured to one another by standard means known in the art such that the layer of fluffed wood pulp is between a substantial portion of the topsheet and backsheet layers.

In order to provide a better understanding of the present invention, the following examples primarily illustrate certain more specific details thereof. In the following examples, the characteristics of the pulp were determined by the following tests:

Pre-poured Saturated Drainage (PSD) Test

In this test, a pulp is formed into an absorbent pad, saturated with liquid to form a pre-poured pad and the pad is drained to simulate a used diaper. Liquid is drained through this pre-poured pad with a Canadian Standard Freeness (CSF) test device as described in TAPPI-T 227 om-85, and the side volume drained from the device is used to measure the rate of liquid transport in the pad.

To conduct the test, a sheet of pulp to be tested is first shred in a Kamas mill into fluff using standard fluffing conditions. The fluff is air-dried and 12.0 grams (equivalent to 11.2 grams of oven-dried pulp) are weighed and mixed in about 600 mL of distilled or de-ionized water using a LIGHTNIN Mixer or a TAPPI/British Disintegrator for 10 seconds. The resulting volume should be less than 1000 mL.

All of the mixed fiber is then poured into the top chamber of the CSF test device and the water is drained and collected thereby forming a pad of the fibers. Free water is gently squeezed from the pad and collected until only a fine mist is being sprayed out (about 3 to 10 squeezes) using the rubber bulb on the top of the CSF tester. The water collected and squeezed from the pad is then poured onto the pad being careful not to disturb the pad by the flow of water. The water dripping through the pad is collected in CSF chamber. This water is discarded and any excess water is then removed from the pad using the rubber bulb as before.

Next, 667 mL of clean water at room temperature (25° C.) is poured through the pad into the CSF chamber being careful not to disturb the pad. Water is drained from the CSF chamber while collecting and measuring the volume of water from the side opening of the CSF device. Excess water is again removed from the pad using the rubber bulb. The foregoing step is repeated until the 3 most recent volumes collected from the pad are within 10 mL of each other.

After completing the test, the bottom of the CSF chamber is closed and removed from its holder. The pad is gently removed from the chamber and placed flat on a blotter in order to dry completely. Drying the pad may take 1 to 2 nights. After drying, the height of the pad is measured and recorded.

Strike-through Acquisition Test

This test is used to simulate the absorption rate of a diaper containing several wettings and the tendency for the wet diaper to re-wet the baby. To obtain the strike-through acquisition weight and time, pulp is first shredded in a Kamas hammer-mill into fluff. An air-laid fluff pulp pad is made from 30 grams of the shredded pulp. A total of 9 pads each having a diameter of 5 inches may be made on a Demand-Wettability pad former or rectangular pads, 9 inches long by 4 inches wide can be made on an air-laid pad former. The pads made on the pad former are then weaved together in a line of 3 piles of 3 pads each with a 1 inch overlap. For pads made containing super-absorbing polymer (SAP), 10 grams of the SAP is sprinkled on the top of the bottom pad before covering the bottom pad with the other pads.

The constructed pad is then placed in the center of a 4 inch deep bowl having a 9 inch upper diameter and a 4 inch lower diameter. An amount of liquid equal to twice the pad weight is poured into the center of the pad and timing is begun. The time required to absorb all of the free liquid above the pad is recorded as the strike-through acquisition time. This procedure is repeated two times at 20 minute intervals to simulate second and third wettings.

After another 20 minute period, 5 grams of dry shredded fluff pulp are pressed onto the center of the pad by hand or by use of a blotter and an 8 pound weight. After 15 seconds, the blotting pulp is removed and weighed. The weight gained by the blotting pulp is recorded as the re-wet weight.

Finally, the pad is re-wet a fourth time using an amount of water equal to twice the initial pad weight plus the amount of water removed in the blotting step. The fourth strike-through acquisition time is the time reported in the examples.

EXAMPLE 3

Several samples of 133 oven dried grams of bleached kraft softwood where mixed with water to form slurries each weighing 392 grams and having consistencies of 33.9%. The fluffed wood pulp is produced according to the method detailed in Example 2 above. The reaction temperature was 74° C. and the and the slurry was treated for two minutes with a caustic solution prepared to provide a slurry consistency of 8%. Various concentrations of NaOH solutions were used. A pre-poured saturated drainage (PSD) test was performed on each sample. The PSD test is a measure of the liquid transport capability of fluff. A higher value indicates a higher transport capability. Summaries of the results are listed in Table 1.

TABLE 1

| NaOH in Slurry (g/L) | H$_2$O added (grams) | Solid NaOH (grams) | PSD (mL) |
|---|---|---|---|
| 0 | 1271 | 0 | 430 |
| 164 | 1055 | 216 | 480 |
| 199 | 1017 | 254 | 490 |
| 223 | 992 | 279 | 500 |
| 248 | 967 | 304 | 490 |
| 331 | 890 | 381 | 510 |
| 426 | 814 | 457 | 520 |

For caustic concentrations in the range of 164 to 426 grams per liter, there was dramatic increase in PSD volumes as compared to untreated fibers.

EXAMPLE 4

Several samples of 187.5 oven dried grams of bleached kraft softwood fibers were mixed into slurries weighing 553 grams and having consistencies of 33.9 wt. %. The fluffed wood pulp was produced generally in accordance with the method detailed above in Example 2. The reaction temperature was 23° C., and the reaction was conducted for two minutes in the presence of 1700 milliliters of white liquor, 1700 milliliters of $Na_2S$ and water and 1700 milliliters of white liquor containing 100 grams of sodium sulfide. A PSD test was performed on each sample. Summaries of the results are listed in Table 2.

TABLE 2

| White liquor (mL) | $Na_2S*9H_2O$ (grams) | $H_2O$ (mL) | PSD (mL) |
|---|---|---|---|
| 1700 | 0 | 0 | 500 |
| 1700 | 100 | 0 | 505 |
| 0 | 100 | 1700 | 385 |
| 0 | 0 | 1700 | 390 |

The white liquor treatments were effective in improving the liquid transport properties of the processed fibers.

EXAMPLE 5

Bleached kraft softwood pulp was processed generally in accordance with the method described above in Example 2 and various properties of the recovered fibers were compared against a sample of the virgin bleached kraft softwood fibers, a sample with 50 wt. % fluffed wood pulp and 50 wt. % virgin fibers and a sample containing 100 wt. % fluffed wood pulp. Summaries of the results are listed in Table 3. The Acquisition Tests were performed on pulp containing no super-absorbing polymer (SAP).

TABLE 3

| Pulp Identification | Virgin Pulp | 50 wt. % Blend | 100 wt. % Treated |
|---|---|---|---|
| Scan Absorbency Test | | | |
| Absorbent time (sec.) | 3.0 | 3.3 | 2.7 |
| Capacity (g/g) | 10.5 | 10.6 | 10.5 |
| Specific Fluff vol. (cc/g) | 20.6 | 20.5 | 18.5 |
| Basket Sink Test | | | |
| Sink Time (sec.) | 2.3 | 2.1 | 2.0 |
| Absorptive capacity (g/g) | 20.9 | 19.6 | 17.6 |
| Demand Wettability Test | | | |
| Initial Absorbance (sec./10 mL) | 28.0 | 28.0 | 26.0 |
| Absorptive Capacity (g/g) | 11.8 | 12.5 | 12.3 |
| PSD Drainage Test (mL) | 360.0 | 425.0 | 510.0 |
| Acquisition Test no SAP | | | |
| 4th wetting (sec.) | 38.0 | 15.0 | 9.0 |
| Re-wet weight (g) | 38.0 | 34.0 | 37.0 |

The results indicate that even in a 50 wt. % blend, the fluffed wood pulp fibers are superior to the virgin kraft softwood fibers as shown by the PSD test.

In the foregoing example, the test procedures which were used are as follows:

Scan Absorbency Test

The scan absorbency test is based on the Scandinavian Pulp and Paper and Board Testing Committee Standards designated as SCAN-C33:80. In the procedure, fluffed pulp (3.0 grams) was used to form an absorbent pad in a fluff pad former and the pad was placed on an absorption and bulk tester (both of which instruments are available from Papirindustriens Forskningsinstitutt of Oslo, Norway). A 500 gram load was then placed on top of the pad and the plexiglas mold used to form the pad was removed. The screen on the base of the pad holder was pressed up against the pad to permit uniform wetting of the pad during scan testing.

After measuring and recording the pad caliper, the liquid reservoir of the tester was filled with 0.9 wt. % saline solution. The reservoir was then raised so that the base of the sample pad barely reached the reservoir. At the moment the test pad came into contact with the saline solution, the timer was started. When the saline solution had penetrated the sample pad, the timer was stopped and the absorption time in seconds was recorded.

Next, the sample pad was allowed to absorb liquid for an additional 30 seconds and the reservoir was then lowered so that the pad could drain for 30 seconds. Finally, the load was removed from the pad and the saturated sample pad was weighed. In order to calculate the specific fluff volume and absorptive capacity, the following equations were used:

$$\text{Specific volume } (cm^3/\text{grams}) = \text{caliper } (cm) \times 6.55$$

$$\text{Absorptive Capacity (gram/gram)} = \frac{\text{Total solution absorbed (g)}}{3 \text{ grams of pulp}}$$

Demand Wettability Test

The Demand Wettability Test was adapted from the March 1974 INDA Technical Symposium paper entitled "Demand Wettability: A method for Measuring Absorbency Characteristics of Fabrics." In the test, a pulp fluff pad weighing 3 grams was formed and then pressed to a caliper of 0.135 inches using a hydraulic press such as a Carver Model C hydraulic press.

Next, the buret of a Demand Wettability tester (available from Scientific Machines & Company of Middlesex, NJ) was filled with 0.9 wt. % saline solution and the tester was set on zero. The pressed pad was placed on the demand wettability tester, carefully centering the pad over the delivery orifice. A six inch diameter stainless steel plate and a weight, totalling 322 grams, was placed on top of the pad.

The demand flow was initiated by opening the stopcock on the buret. The time, in seconds, when each 5 milliliters of liquid was drawn from the buret was recorded until the flow through the pad stopped. The final buret reading was then recorded. A minimum of 3 pads per fluff sample were tested. The absorptive capacity was calculated by the following formula:

$$\text{Absorptive capacity (g.sol./g.pulp)} = \frac{\text{Total solution absorbed (g)}}{3 \text{ grams of pulp}}$$

Basket Sink Test

In this test, a known weight of pulp fluff was allowed to sink in a saline solution. The fluff integrity was maintained by use of a wire basket and nonwoven tissue. In the test, 5 grams of pulp fluff were weighed and added evenly to a standard wire basket made from 22 gauge copper wire having a diameter of 5 centimeters, a length of 8 centimeters and containing wire rings spaced at 2 centimeter intervals. The basket weighed about 4 grams and was lined with tissue pieces each measuring 8 centimeters by 20 centimeters.

The basket was held horizontally above a 2-liter beaker containing 1400 milliliters of 0.9 wt. % saline solution. Next the basket was evenly lowered until the basket touched the saline solution. When the basket was released into the beaker, the timer was started.

When the basket became completely submerged, the timer was stopped and the time was recorded. The basket was allowed to remain submerged for 15 seconds after stopping the timer.

Next the basket was removed from the saline solution and tilted at a 45° angle for 15 seconds in order to drain. The wet basket of pulp was placed in a tared container and weighed. After subtracting the weight of the fluff and basket, the weight was divided by 5 and reported as absorptive capacity in grams of saline solution per gram of pulp. Multiple samples of the same fluffed pulp were tested (3 to 5 samples).

EXAMPLE 6

Sample of 66.4 oven dry grams of unbleached pine pulps from Mobile, Ala., and unbleached hardwood pulps from Natchez, Miss. were prepared, and treated with a caustic solution at 8% consistency. Summaries of the results are listed in Table 4.

TABLE 4

| Pulp # | Temp. (° C.) | NaOH Treatment (g/L) | PSD (mL) | Kappa | Brightness Reverted |
|---|---|---|---|---|---|
| Unbleached Pine | | | | | |
| 1 | 23 | 0 | 290 | 32.6 | — |
| 2 | 40 | 148 | 470 | 29.5 | 14.3 |
| 3 | 40 | 170 | 475 | 29.8 | 13.9 |
| 4 | 23 | 265 | 495 | — | — |
| Unbleached Hardwood | | | | | |
| 5 | 23 | 0 | 0 | 15.3 | — |
| 6 | 37 | 145 | 255 | 9.4 | 27.3 |
| 7 | 39 | 175 | 265 | 9.4 | 25.4 |
| Bleached Hardwood | | | | | |
| 8 | 23 | 170 | 355 | — | — |

The improved properties of the NaOH treated unbleached pulps confirm the improved fluid transport properties of the fluffed wood pulp as compared to the untreated pulp. Furthermore, the absorbency and drainage advantages of the fluffed wood pulp persist upon bleaching as illustrated by Pulp #8. As can be seen, the treatment process may also have the advantage of removing lignin and reducing the kappa value of the unbleached pulps, with some brightness increase.

Thus, the personal hygiene articles of the present invention contain pulp processed with chemicals commonly found in the industry. Furthermore, the chemicals used to form the fluffed pulp may be easily removed by simple water washing. Another advantage of the invention is that the improved absorbency pulp may be made with inexpensive chemicals using relatively short reaction times. The resulting fluffed wood pulp may be used without additives as an absorbent sublayer or it may be combined with other super-absorbing compounds and fibers for increased absorbency.

Although this specification discloses particular embodiments of the invention, these examples merely describe illustrations of the invention. Those skilled in the art may recognize numerous rearrangements, modifications and substitutions of the invention within the spirit and scope of the appended claims.

What is claimed is:

1. A personal hygiene article for absorbing fluids, the article comprising:
    at least one fluid permeable topsheet layer and at least one substantially fluid impermeable backsheet layer; and
    an absorbent sublayer material interposed between the topsheet layer and the backsheet layer, the sublayer material containing at least about 10 wt. % of fluffed wood fiber pulp comprising base-treated and dry-shredded wood fiber pulp having a pre-poured saturated drainage (PSD) capacity of greater than 400 mL.

2. The article of claim 1 wherein the sublayer contains about 50 wt. % of fluffed wood pulp and about 50 wt. % unprocessed fibers.

3. The article of claim 1 wherein the sublayer contains at least about 10 wt. % of fluffed wood pulp and from about 0 to about 90 wt. % of a super-absorbing polymer.

4. The article of claim 1 wherein the fluffed wood pulp is further characterized by having a strike-through acquisition re-wet weight of less than about 40 grams.

5. The article of claim 1 wherein the fluffed wood pulp is a mercerized wood pulp.

6. A disposable, highly absorbent diaper comprising:
    at least one fluid permeable topsheet layer;
    at least one fluid impervious backsheet layer coterminous with said topsheet layer; and
    at least one absorbent sublayer between said at least one topsheet layer and said at least one backsheet layer, said absorbent layer containing at least about 10 wt. % of fluffed wood fiber pulp composed of cellulose II fibers comprising base-treated and dry-shredded wood fiber pulp having a pre-poured saturated drainage (PSD) capacity of greater than 400 mL.

7. The diaper of claim 6 wherein the sublayer contains about 50 wt. % of fluffed wood pulp and about 50 wt. % unprocessed fibers.

8. The diaper of claim 6 wherein the sublayer contains from about 10 to about 100 wt. % of fluffed wood pulp and from about 0 to about 90 wt. % of a super-absorbing polymer.

9. The diaper of claim 6 wherein the fluffed wood pulp is further characterized as having a strike-through acquisition re-wet weight of less than about 40 grams.

10. The diaper of claim 6 wherein the fluffed wood pulp is a mercerized wood pulp.

11. A super-absorbent sanitary napkin comprising:
    at least one fluid permeable topsheet layer;
    at least one fluid impervious backsheet layer coterminous with said topsheet layer; and
    at least one absorbent sublayer between said at least one topsheet layer and said at least one backsheet layer, said at least one absorbent layer containing at least about 10 wt. % of fluffed wood fiber pulp comprising base-treated and dry-shredded wood fiber pulp having a pre-poured saturated drainage (PSD) capacity of greater than 400 mL.

12. The sanitary napkin of claim 11 wherein the sublayer contains about 50 wt. % of fluffed wood pulp and about 50 wt. % unprocessed fibers.

13. The sanitary napkin of claim 11 wherein the sublayer contains from about 10 to about 100 wt. % of fluffed wood pulp and from about 0 to about 90 wt. % of a super-absorbing polymer.

14. The sanitary napkin of claim 11 wherein the fluffed wood pulp is further characterized as having a strike-through acquisition re-wet weight of less than about 40 grams.

15. The sanitary napkin of claim 11 wherein the fluffed wood pulp is a mercerized wood pulp.

* * * * *